(12) United States Patent
Imai et al.

(10) Patent No.: US 12,037,315 B2
(45) Date of Patent: Jul. 16, 2024

(54) PRODUCTION METHOD FOR 4-HYDROXY-2-METHYLBENZOIC ACID

(71) Applicant: HONSHU CHEMICAL INDUSTRY CO., LTD., Tokyo (JP)

(72) Inventors: Ryota Imai, Wakayama (JP); Kazuhito Ashida, Wakayama (JP)

(73) Assignee: HONSHU CHEMICAL INDUSTRY CO., LTD., Tokyo (JP)

( * ) Notice: Subject to any disclaimer, the term of this patent is extended or adjusted under 35 U.S.C. 154(b) by 451 days.

(21) Appl. No.: 17/433,192

(22) PCT Filed: Mar. 3, 2020

(86) PCT No.: PCT/JP2020/008837
§ 371 (c)(1),
(2) Date: Aug. 23, 2021

(87) PCT Pub. No.: WO2020/179769
PCT Pub. Date: Sep. 10, 2020

(65) Prior Publication Data
US 2022/0127216 A1    Apr. 28, 2022

(30) Foreign Application Priority Data
Mar. 6, 2019   (JP) .................................. 2019-040453

(51) Int. Cl.
*C07C 51/15*    (2006.01)
*C07C 51/377*   (2006.01)

(52) U.S. Cl.
CPC ............ *C07C 51/15* (2013.01); *C07C 51/377* (2013.01)

(58) Field of Classification Search
CPC ....... C07C 51/15; C07C 51/377; C07C 65/03; C07B 61/00
See application file for complete search history.

(56) References Cited

U.S. PATENT DOCUMENTS

| | | | |
|---|---|---|---|
| 3,655,744 A | 4/1972 | Yasuhara et al. | |
| 4,663,478 A | 5/1987 | Hirai et al. | |
| 4,996,354 A * | 2/1991 | Neumann ............... | C07C 51/15 562/424 |
| 2006/0052632 A1 | 3/2006 | Ueno et al. | |
| 2006/0183939 A1 | 8/2006 | Ueno et al. | |

FOREIGN PATENT DOCUMENTS

| | | | |
|---|---|---|---|
| CN | 1684935 A | 10/2005 | |
| CN | 102050729 A | 5/2011 | |
| CN | 106432159 A * | 2/2017 | ........... C07D 307/80 |
| CN | 109096099 A | 12/2018 | |
| JP | S63156746 A | 6/1988 | |
| JP | H0517397 A | 1/1993 | |
| JP | H07213295 A | 8/1995 | |
| WO | 8503701 A1 | 8/1985 | |
| WO | 2004078693 A1 | 9/2004 | |

OTHER PUBLICATIONS

CN10432159 (A) Yang Yan et al., Novel benzofuran derivative as well as preparation method and application thereof, English translation, 15 pages (Year: 2017).*
International Search Report (ISR) mailed Jun. 9, 2020, issued for International application No. PCT/JP2020/008837. (2 pages).
Itoh et al. Dealkylation of Alkylbenzenes Induced by Aluminum Chloride, The Journal of the Society of Chemical Industry, Japan, 1967, pp. 918-921, vol. 70, No. 6. (4 pages).
A First Office Action issued by the State Intellectual Property Office of China on Apr. 21, 2023, for Chinese counterpart application No. 202080013957.3 (6 pages).
International Preliminary Report on Patentability, dated Aug. 25, 2021, for corresponding international application PCT/JP2020/008837 (1 page).
Notification Concerning Transmittal of International Preliminary Report on Patentability, mailed Sep. 16, 2021, for corresponding international application PCT/JP2020/008837 (1 page).
Notification of Transmittal of Translation of the International Preliminary Report on Patentability, mailed Sep. 16, 2021, for corresponding international application PCT/JP2020/008837 (1 page).
Written Opinion of the International Searching Authority, mailed Jun. 9, 2020, for corresponding international application PCT/JP2020/008837 (4 page).

* cited by examiner

*Primary Examiner* — Yate' K Cutliff
(74) *Attorney, Agent, or Firm* — Law Office of Katsuhiro Arai

(57) ABSTRACT

An object is to provide a novel production method for 4-hydroxy-2-methylbenzoic acid that is suitable for industrial use. As a solution, a production method for 4-hydroxy-2-methylbenzoic acid that includes performing a step (I) of reacting a compound represented by general formula (1) with carbon dioxide to obtain a compound represented by general formula (2), and then a step (II) of dealkylating the compound represented by general formula (2), is provided.

2 Claims, No Drawings

PRODUCTION METHOD FOR 4-HYDROXY-2-METHYLBENZOIC ACID

CROSS-REFERENCE TO RELATED APPLICATIONS

This application is the U.S. National Phase under 35 U.S.C. § 371 of International Application PCT/JP2020/008837, filed Mar. 3, 2020, which claims priority to Japanese Patent Application No. JP2019-040453, filed Mar. 6, 2019. The International Application was published under PCT Article 21(2) in a language other than English.

TECHNICAL FIELD

The present invention relates to a novel production method for 4-hydroxy-2-methylbenzoic acid that includes a step of introducing a carboxyl group into a phenol.

BACKGROUND ART

The Kolbe-Schmitt reaction is known as a reaction for introducing a carboxyl group into a phenol. The Kolbe-Schmitt reaction, which is a reaction using an alkali metal phenoxide and carbon dioxide, often requires high-temperature and high-pressure reaction conditions, specifically, a reaction temperature of about 200° C. and a reaction pressure of about several hundred to several thousand kilopascals. Thus, the Kolbe-Schmitt reaction requires dedicated equipment. In addition, the Kolbe-Schmitt reaction shows low reaction selectivity, and it is often difficult to achieve carboxylation at a target position on a benzene ring. In particular, in the case of an alkyl-substituted phenol, desired regioselectivity can hardly be exhibited due to steric and electronic factors of the substituent.

4-Hydroxy-2-methylbenzoic acid, despite being useful as a pharmaceutical raw material or a resin raw material, has a problem in that when an attempt is made to introduce a carboxyl group at the para position of a phenolic hydroxyl group, the presence of an adjacent methyl group reduces the selectivity of carboxylation. Various approaches for increasing the reaction selectivity in the introduction of a carboxyl group have been reported.

For example, PTL 1 states that a mixture of 4-hydroxy-2-methylbenzoic acid and 4-methylsalicylic acid is obtained in 18 mol % yield (relative to m-cresol) by reacting potassium carbonate and carbon monoxide at 235° C. and 8.5 MPa using potassium salt of m-cresol as a starting material, but this reaction cannot be said to be highly selective.

PTL 2 states that the para position of a phenolic hydroxyl group can be carboxylated with high selectivity by reacting m-cresol as a starting material with carbon tetrachloride in an aqueous sodium hydroxide solution using copper powder and a copolymer of cyclodextrin and epichlorohydrin as catalysts. However, the carbon tetrachloride for use is an ozone depleting substance, a large amount of aqueous sodium hydroxide solution is used, and, furthermore, the catalysts are used in an amount comparable to that of the raw material; these reaction conditions lack practicality for industrial production methods.

Furthermore, PTL 3 states that 4-hydroxy-2-methylbenzoic acid can be selectively synthesized by oxidizing a methyl group at the para position of a phenolic hydroxyl group using 3,4-xylenol as a starting material and *Pseudomonas putida*, a microorganism. However, dedicated special equipment is required for the management, reaction, and treatment of the microorganism, and thus this synthesis is not practical as an industrial production method.

CITATION LIST

Patent Literature

PTL 1: U.S. Pat. No. 3,655,744
PTL 2: International Publication No. 1985/03701
PTL 3: Japanese Unexamined Patent Application Publication No. 07-213295

SUMMARY OF INVENTION

Technical Problem

The present invention has been made in view of the circumstances described above, and an object thereof is to provide a novel production method for 4-hydroxy-2-methylbenzoic acid that is suitable for industrial use.

Solution to Problem

The present inventors have intensively studied in view of the above problems of the related art and found that by performing a step (I) of carrying out the Kolbe-Schmitt reaction using carbon dioxide and a compound having a removable alkyl group and represented by general formula (1), and then a step (II) of dealkylation, 4-hydroxy-2-methylbenzoic acid, in which the para position of a phenolic hydroxyl group is carboxylated with high selectivity, is obtained, thereby completing the present invention practiced under mild reaction conditions which are suitable for industrial use.

The present inventors have also found that using an aprotic polar solvent as a reaction solvent in the step (I) further improves reaction efficiency.

The present invention is as follows.

1. A production method for 4-hydroxy-2-methylbenzoic acid includes performing a step (I) of reacting a compound represented by general formula (1) below with carbon dioxide to obtain a compound represented by general formula (2) below, and then a step (II) of dealkylating the compound represented by general formula (2).

[Chem. 1]

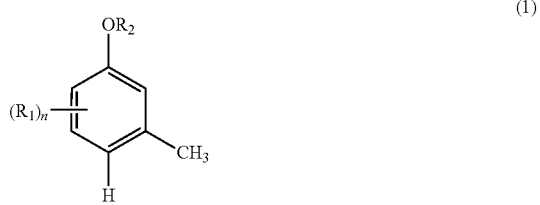

(1)

(In formula, $R_1$ represents a branched alkyl group having 3 to 8 carbon atoms or a cyclic alkyl group having 5 to 6 carbon atoms, $R_2$ represents a hydrogen atom or an alkali metal, and n represents an integer of 1 to 3.)

[Chem. 2]

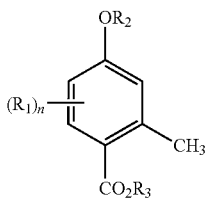

(2)

(In formula, $R_1$, $R_2$, and n are as defined in general formula (1), and $R_3$ represents a hydrogen atom or an alkali metal.)

2. The production method according to 1, in which an aprotic polar solvent is used as a reaction solvent in the step (I).

Advantageous Effects of Invention

The production method for 4-hydroxy-2-methylbenzoic acid according to the present invention is very useful in that the reaction proceeds under very mild reaction conditions as compared to the Kolbe-Schmitt reaction known in the art, and thus dedicated equipment or a reactor for carrying out a high-temperature and high-pressure reaction is not required.

In addition, the production method according to the present invention can selectively provide 4-hydroxy-2-methylbenzoic acid with efficiency and thus is a very advantageous method as an industrial production method.

In particular, the use of an aprotic polar solvent as a reaction solvent in the step (I) further improves reaction efficiency, which is industrially useful.

DESCRIPTION OF EMBODIMENTS

Hereinafter, the present invention will be described in detail.

As shown by the following reaction formula, a production method according to the present invention is a production method including performing a step (I) of reacting a compound represented by general formula (1) with carbon dioxide to obtain a compound represented by general formula (2) below, and then performing a step (II) of dealkylating the compound represented by general formula (2).

[Chem. 3]

(In the reaction formula, $R_1$, $R_2$, $R_3$, and n are as defined in general formulae (1) and (2) above.)

<Regarding Step (I)>

The reaction of the step (I) is a step of reacting the compound represented by general formula (1) with carbon dioxide to obtain the compound represented by general formula (2).

(Compound Represented by General Formula (1))

In the production method according to the present invention, the compound represented by general formula (1) is used as a starting material.

$R_1$ in general formula (1) represents a branched alkyl group having 3 to 8 carbon atoms or a cyclic alkyl group having 5 to 6 carbon atoms, and specific examples include isopropyl, isobutyl, s-butyl, t-butyl, 1-methylbutyl, 1,1-dimethylpropyl, 1-methylpentyl, 1,1-dimethylbutyl, 1-methyl-1-ethylpropyl, 1-methylhexyl, 1,1-dimethylpentyl, 1-methyl-1-ethylbutyl, 1-methylheptyl, 1,1-dimethylhexyl, 1-methyl-1-ethylpentyl, 1,1-dimethyl-3,3-dimethylbutyl, cyclopentyl, and cyclohexyl. Of these, tertiary alkyl groups, specifically, t-butyl, 1,1-dimethylpropyl, 1,1-dimethylbutyl, 1-methyl-1-ethylpropyl, 1,1-dimethylpentyl, 1-methyl-1-ethylbutyl, 1,1-dimethylhexyl, 1-methyl-1-ethylpentyl, and 1,1-dimethyl-3,3-dimethylbutyl are preferred, t-butyl and 1,1-dimethyl-3,3-dimethylbutyl are more preferred, and t-butyl is particularly preferred. In view of the orientation of the Kolbe-Schmitt reaction, the site of substitution of $R_1$ in general formula (1) is preferably the ortho position of the hydroxyl group, and is more preferably also the para position of the methyl group in order to obtain 4-hydroxy-2-methylbenzoic acid, which is an object, with high selectivity.

The number n of $R_1$'s in general formula (1) is an integer of 1 to 3. When n is 2 or 3, $R_1$'s need not necessarily be the same substituent and may be different substituents, but are preferably substituents of the same type from the standpoint of ease of introduction and dealkylation. For ease of dealkylation reaction, n is preferably 1.

$R_2$ in general formula (1) represents a hydrogen atom or an alkali metal. Specific examples of the alkali metal include lithium, sodium, and potassium. Of these, sodium and potassium are preferred, and potassium is particularly preferred.

Preferred examples of the compound represented by general formula (1) include 2-isopropyl-5-methylphenol, 2-(1-methylpropyl)-5-methylphenol, 2-t-butyl-5-methylphenol, 2-(1-methylbutyl)-5-methylphenol, 2-(1,1-dimethylpropyl)-5-methylphenol, 2-(1-methylpentyl)-5-methylphenol, 2-(1,1-dimethylbutyl)-5-methylphenol, 2-(1-methyl-1-ethylpropyl)-5-methylphenol, 2-(1-methylhexyl)-5-methylphenol, 2-(1,1-dimethylpentyl)-5-methylphenol, 2-(1-methyl-1-ethylbutyl)-5-methylphenol, 2-(1-methylheptyl)-5-methylphenol, 2-(1,1-dimethylhexyl)-5-methylphenol, 2-(1-methyl-1-ethylpentyl)-5-methylphenol, 2-(1,1-dimethyl-3,3-dimethylbutyl)-5-methylphenol, 2-cyclopentyl-5-methylphenol, 2-cyclohexyl-5-methylphenol, 2,6-diisopropyl-3-methylphenol, 2,6-di-t-butyl-3-methylphenol, sodium salt of 2-isopropyl-5-methylphenol, sodium salt of 2-(1-methylpropyl)-5-methylphenol, sodium salt of 2-t-butyl-5-methylphenol, sodium salt of 2-(1-methylbutyl)-5-methylphenol, sodium salt of 2-(1,1-dimethylpropyl)-5-methylphenol, sodium salt of 2-(1-methylpentyl)-5-methylphenol, sodium salt of 2-(1,1-dimethylbutyl)-5-methylphenol, sodium salt of 2-(1-methyl-1-ethylpropyl)-5-methylphenol, sodium salt of 2-(1-methylhexyl)-5-methylphenol, sodium salt of 2-(1,1-dimethylpentyl)-5-methylphenol, sodium salt of 2-(1-methyl-1-ethylbutyl)-5-methylphenol, sodium salt of 2-(1-methylheptyl)-5- methylphenol, sodium salt of 2-(1,1-dimethylhexyl)-5-methylphenol, sodium salt of 2-(1-methyl-1-ethylpentyl)-5-methylphenol, sodium salt of 2-(1,1-dimethyl-3,3-dimethylbutyl)-5-methylphenol, sodium salt of 2-cyclopentyl-5-methylphenol, sodium salt of 2-cyclohexyl-5-methylphenol, sodium salt of 2,6-diisopropyl-3-methylphenol, sodium salt of 2,6-di-t-butyl-3-methylphenol, potassium salt of 2-isopropyl-5-methylphenol, potassium salt of 2-(1-methylpropyl)-5-methylphenol, potassium salt of 2-t-butyl-5-methylphenol, potassium salt of 2-(1-methylbutyl)-5-methylphenol, potassium salt of 2-(1,1-dimethylpropyl)-5-methylphenol, potassium salt of 2-(1-methylpentyl)-5-methylphenol, potassium salt of 2-(1,1-dimethylbutyl)-5-methylphenol, potassium salt of 2-(1-methyl-1-ethylpropyl)-5-methylphenol, potassium salt of 2-(1-methylhexyl)-5-methylphenol, potassium salt of 2-(1,1-dimethylpentyl)-5-methylphenol, potassium salt of 2-(1-methyl-1-ethylbutyl)-5-methylphenol, potassium salt of 2-(1-methylheptyl)-5-methylphenol, potassium salt of 2-(1,1-dimethylhexyl)-5-methylphenol, potassium salt of 2-(1-methyl-1-ethylpentyl)-5-methylphenol, potassium salt of 2-(1,1-dimethyl-3,3-dimethylbutyl)-5-methylphenol, potassium salt of 2-cyclopentyl-5-methylphenol, potassium salt of 2-cyclohexyl-5-methylphenol, potassium salt of 2,6-diisopropyl-3-methylphenol, and potassium salt 2,6-di-t-butyl-3-methylphenol. Of these, 2-t-butyl-5-methylphenol, 2-(1,1-dimethylpropyl)-5-methylphenol, 2-(1,1-dimethylbutyl)-5-methylphenol, 2-(1-methyl-1-ethylpropyl)-5-methylphenol, 2-(1,1-dimethylpentyl)-5-methylphenol, 2-(1-methyl-1-ethylbutyl)-5-methylphenol, 2-(1,1-dimethylhexyl)-5-methylphenol, 2-(1-methyl-1-ethylpentyl)-5-methylphenol, 2-(1,1-dimethyl-3,3-dimethylbutyl)-5-methylphenol, 2,6-di-t-butyl-3-methylphenol, sodium salt of 2-t-butyl-5-methylphenol, sodium salt of 2-(1,1-dimethylpropyl)-5-methylphenol, sodium salt of 2-(1,1-dimethylbutyl)-5-methylphenol, sodium salt of 2-(1-methyl-1-ethylpropyl)-5-methylphenol, sodium salt of 2-(1,1-dimethylpentyl)-5-methylphenol, sodium salt of 2-(1-methyl-1-ethylbutyl)-5-methylphenol, sodium salt of 2-(1,1-dimethylhexyl)-5-methylphenol, sodium salt of 2-(1-methyl-1-ethylpentyl)-5-methylphenol, sodium salt of 2-(1,1-dimethyl-3,3-dimethylbutyl)-5-methylphenol, sodium salt of 2,6-di-t-butyl-3-methylphenol, potassium salt of 2-t-butyl-5-methylphenol, potassium salt of 2-(1,1-dimethylpropyl)-5-methylphenol, potassium salt of 2-(1,1-dimethylbutyl)-5-methylphenol, potassium salt of 2-(1-methyl-1-ethylpropyl)-5-methylphenol, potassium salt of 2-(1,1-dimethylpentyl)-5-methylphenol, potassium salt of 2-(1-methyl-1-ethylbutyl)-5-methylphenol, potassium salt of 2-(1,1-dimethylhexyl)-5-methylphenol, potassium salt of 2-(1-methyl-1-ethylpentyl)-5-methylphenol, potassium salt of 2-(1,1-dimethyl-3,3-dimethylbutyl)-5-methylphenol, and potassium salt of 2,6-di-t-butyl-3-methylphenol, each having a tertiary alkyl group, are preferred; 2-t-butyl-5-methylphenol, 2-(1,1-dimethyl-3,3-dimethylbutyl)-5-methylphenol, sodium salt of 2-t-butyl-5-methylphenol, sodium salt of 2-(1,1-dimethyl-3,3-dimethylbutyl)-5-methylphenol, potassium salt of 2-t-butyl-5-methylphenol, and potassium salt of 2-(1,1-dimethyl-3,3-dimethylbutyl)-5-methylphenol are more preferred; and 2-t-butyl-5-methylphenol, sodium salt of 2-t-butyl-5-methylphenol, and potassium salt of 2-t-butyl-5-methylphenol are particularly preferred.

Furthermore, when a mixture of the compound represented by general formula (1) and a salt thereof is used as a starting material, the amount of the salt in which $R_2$ is an alkali metal is preferably 1.0 mol or more relative to 1 mol of the compound in which $R_2$ is hydrogen. The upper limit of the amount of the salt is preferably 2.0 mol or less, more preferably 1.5 mol or less, still more preferably 1.3 mol or less.

(Carbon Dioxide)

The reaction of the step (I) is carried out in a state where carbon dioxide gas is present in a reaction vessel. The carbon dioxide gas may be blown into the reaction vessel containing the compound represented by general formula (1) in a continuous or intermittent manner, and is preferably blown in a continuous manner. The carbon dioxide gas may be blown into a reaction solution containing the compound represented by general formula (1) or may be blown to a space defined by the reaction solution and the reaction vessel. The reaction may be carried out under normal pressure or increased pressure depending on the equipment, and is preferably carried out under a carbon dioxide pressure in the range of atmospheric pressure to 50.0 kgf/cm$^2$.

(Reaction Solvent)

The reaction solvent used in the reaction of the step (I) is preferably an aprotic polar solvent because the reaction efficiency is further improved. Specific examples of the aprotic polar solvent include 1,3-dimethyl-2-imidazolidinone, acetonitrile, dimethylformamide, dimethylacetamide, N-methyl-2-pyrrolidone, dimethylsulfoxide, sulfolane, propylene carbonate, hexamethylphosphoric triamide, N,N'-dimethylpropyleneurea, and tetramethylurea. Of these, those which are highly stable even in the presence of an alkali metal salt represented by general formula (1) are preferred, and 1,3-dimethyl-2-imidazolidinone, N-methyl-2-pyrrolidone, dimethylacetamide, dimethylformamide, and dimethylsulfoxide are preferred. These may be used in any combination. The amount of aprotic polar solvent used is not particularly limited, and in terms of economic efficiency, the amount is typically 0.1 or more times, preferably 0.5 to 100 times, more preferably 1 to 20 times the amount of the compound represented by general formula (1) on a weight basis.

These aprotic polar solvents may be used in combination with another solvent. Any solvent can be used in combination as long as it is inactive in the reaction. For example, aromatic hydrocarbon solvents such as toluene and xylene and linear and cyclic aliphatic hydrocarbon solvents such as hexane and cyclohexane may be used, and the compound represented by general formula (1) used in the reaction may also be used as a solvent. A solvent (solvent azeotropic with water) used to dehydrate the reaction system in obtaining a salt of the compound represented by general formula (1) may be present in the reaction system. Furthermore, these solvents that can be used in combination with the aprotic polar solvents may be used alone or in combination of two or more.

(Reaction Conditions)

The reaction temperature in the step (I) is preferably 20° C. to 100° C., more preferably 50° C. to 90° C., particularly preferably 60° C. to 80° C. The reaction is typically carried out under normal pressure and may be carried out under increased pressure. Although depending on the reaction temperature and other conditions, the reaction time is typically in the range of 1 to 50 hours, preferably in the range of 1 to 40 hours, more preferably in the range of 1 to 30 hours. Furthermore, the reaction of the step (I) is carried out at a reaction temperature of 20° C. to 100° C. and normal pressure using an aprotic polar solvent as a reaction solvent, more preferably carried out at a reaction temperature of 50° C. to 90° C. and normal pressure using an aprotic polar solvent as a reaction solvent, and particularly preferably carried out at a reaction temperature of 60° C. to 80° C. and normal pressure using an aprotic polar solvent as a reaction solvent. These are preferred reaction conditions because the para position of a phenolic hydroxyl group is carboxylated with high selectivity and thus the compound of interest represented by general formula (2) is efficiently obtained.

The progress of the reaction of the step (I) will be hindered if water is present in the reaction system, and thus the reaction system needs to be in a sufficiently dehydrated state. The reaction system may be dehydrated in accordance with a known method. For example, adding a solvent azeotropic with water, such as toluene or ethyl acetate, to distill off a theoretical amount of water, followed by recovering the azeotropic solvent, is an efficient and convenient method. Alternatively, for example, a separately prepared anhydrous salt of the compound represented by general formula (1) may be used. In this case, the reaction solvent for use is preferably dehydrated.

(Post-Reaction Treatment)

After completion of the reaction of the step (I), an acid can be added to thereby precipitate the resulting compound represented by general formula (2) as a crystal solid. Any acid can be used as long as it is an acid defined as a Bronsted acid, and specific examples include inorganic acids such as hydrochloric acid, sulfuric acid, nitric acid, and phosphoric acid; and organic acids such as oxalic acid, citric acid, and acetic acid. In particular, hydrochloric acid and sulfuric acid are preferred. These acids may be used in any combination.

Although depending on the amount of the compound represented by general formula (2) obtained in the step (I), the amount of acid used is preferably 1 or more times, on a molar basis, the amount of the compound represented by general formula (1), a starting material. The acid may be somewhat excessively added.

After the solid precipitated by the addition of an acid is separated by, for example, filtration, washing with water and a solvent is preferably performed. The solvent used here is preferably a solvent that poorly dissolves the precipitated solid and water and can disperse them. Specific examples include aliphatic hydrocarbons typified by hexane, heptane, octane, nonane, decane, undecane, dodecane, ligroin, and kerosene; and aromatic hydrocarbons typified by benzene, toluene, xylene, mesitylene, ethylbenzene, cumene, and naphthalene. These may be used in any combination.

(Regarding Compound Represented by General Formula (2))

An intermediate in the production method according to the present invention is a compound represented by general formula (2).

Specific examples and preferred examples of $R_1$, $R_2$, and n in general formula (2) are the same as those of $R_1$, $R_2$, and n in general formula (1) described above. Specific examples and preferred examples of $R_3$ in general formula (2) are the same as those of $R_2$ in general formula (1) described above. In general formula (2), $R_2$ and $R_3$ may be the same or different, but are preferably the same in terms of efficiency.

Preferred examples of the compound represented by general formula (2) include 5-isopropyl-4-hydroxy-2-methylbenzoic acid, 5-(1-methylpropyl)-4-hydroxy-2-methylbenzoic acid, 5-t-butyl-4-hydroxy-2-methylbenzoic acid, 5-(1-methylbutyl)-4-hydroxy-2-methylbenzoic acid, 5-(1,1-dimethylpropyl)-4-hydroxy-2-methylbenzoic acid, 5-(1-methylpentyl)-4-hydroxy-2-methylbenzoic acid, 5-(1,1-dimethylbutyl)-4-hydroxy-2-methylbenzoic acid, 5-(1-methyl-1-ethylpropyl)-4-hydroxy-2-methylbenzoic acid, 5-(1-methylhexyl)-4-hydroxy-2-methylbenzoic acid, 5-(1,1-dimethylpentyl)-4-hydroxy-2-methylbenzoic acid, 5-(1-methyl-1-ethylbutyl)-4-hydroxy-2-methylbenzoic acid, 5-(1-methylheptyl)-4-hydroxy-2-methylbenzoic acid, 5-(1,1-dimethylhexyl)-4-hydroxy-2-methylbenzoic acid, 5-(1-methyl-1-ethylpentyl)-4-hydroxy-2-methylbenzoic acid, 5-(1,1-dimethyl-3,3-dimethylbutyl)-4-hydroxy-2-methylbenzoic acid, 5-cyclopentyl-4-hydroxy-2-methylbenzoic acid, 5-cyclohexyl-4-hydroxy-2-methylbenzoic acid, 3,5-diisopropyl-4-hydroxy-2-methylbenzoic acid, 3,5-di-t-butyl-4-hydroxy-2-methylbenzoic acid, sodium salt of 5-isopropyl-4-hydroxy-2-methylbenzoic acid, sodium salt of 5-(1-methylpropyl)-4-hydroxy-2-methylbenzoic acid, sodium salt of 5-t-butyl-4-hydroxy-2-methylbenzoic acid, sodium salt of 5-(1-methylbutyl)-4-hydroxy-2-methylbenzoic acid, sodium salt of 5-(1,1-dimethylpropyl)-4-hydroxy-2-methylbenzoic acid, sodium salt of 5-(1-methylpentyl)-4-hydroxy-2-methylbenzoic acid, sodium salt of 5-(1,1-dimethylbutyl)-4-hydroxy-2-methylbenzoic acid, sodium salt of 5-(1-methyl-1-ethylpropyl)-4-hydroxy-2-methylbenzoic acid, sodium salt of 5-(1-methylhexyl)-4-hydroxy-2-methylbenzoic acid, sodium salt of 5-(1,1-dimethylpentyl)-4-hydroxy-2-methylbenzoic acid, sodium salt of 5-(1-methyl-1-ethylbutyl)-4-hydroxy-2-methylbenzoic acid, sodium salt of 5-(1-methylheptyl)-4-hydroxy-2-methylbenzoic acid, sodium salt of 5-(1,1-dimethylhexyl)-4-hydroxy-2-methylbenzoic acid, sodium salt of 5-(1-methyl-1-ethylpentyl)-4-hydroxy-2-methylbenzoic acid, sodium salt of 5-(1,1-dimethyl-3,3-dimethylbutyl)-4-hydroxy-2-methylbenzoic acid, sodium salt of 5-cyclopentyl-4-hydroxy-2-methylbenzoic acid, sodium salt of 5-cyclohexyl-4-hydroxy-2-methylbenzoic acid, sodium salt of 3,5-diisopropyl-4-hydroxy-2-methylbenzoic acid, sodium salt of 3,5-di-t-butyl-4-hydroxy-2-methylbenzoic acid, potassium salt of 5-isopropyl-4-hydroxy-2-methylbenzoic acid, potassium salt of 5-(1-methylpropyl)-4-hydroxy-2-methylbenzoic acid, potassium salt of 5-t-butyl-4-hydroxy-2-methylbenzoic acid, potassium salt of 5-(1-methylbutyl)-4-hydroxy-2-methylbenzoic acid, potassium salt of 5-(1,1-dimethylpropyl)-4-hydroxy-2-methylbenzoic acid, potassium salt of 5-(1-methylpentyl)-4-hydroxy-2-methylbenzoic acid, potassium salt of 5-(1,1-dimethylbutyl)-4-hydroxy-2-methylbenzoic acid, potassium salt of 5-(1-methyl-1-ethylpropyl)-4-hydroxy-2-methylbenzoic acid, potassium salt of 5-(1-methylhexyl)-4-hydroxy-2-methylbenzoic acid, potassium salt of 5-(1,1-dimethylpentyl)-4-hydroxy-2-methylbenzoic acid, potassium salt of 5-(1-methyl-1-ethylbutyl)-4-hydroxy-2-methylbenzoic acid, potassium salt of 5-(1-methylheptyl)-4-hydroxy-2-methylbenzoic acid, potassium salt of 5-(1,1-dimethylhexyl)-4-hydroxy-2-methylbenzoic acid, potassium salt of 5-(1-methyl-1-ethylpentyl)-4-hydroxy-2-methylbenzoic acid, potassium salt of 5-(1,1-dimethyl-3,3-dimethylbutyl)-4-hydroxy-2-methylbenzoic acid, potassium salt of 5-cyclopentyl-4-hydroxy-2-methylbenzoic acid, potassium salt of 5-cyclohexyl-4-hydroxy-2-methylbenzoic acid, potassium salt of 3,5-diisopropyl-4-hydroxy-2-methylbenzoic acid, and potassium salt 3,5-di-t-butyl-4-hydroxy-2-methylbenzoic acid. Of these, 5-t-butyl-4-hydroxy-2-methylbenzoic acid, 5-(1,1-dimethylpropyl)-4-hydroxy-2-methylbenzoic acid, 5-(1,1-dimethylbutyl)-4-hydroxy-2-methylbenzoic acid, 5-(1-methyl-1-ethylpropyl)-4-hydroxy-2-methylbenzoic acid, 5-(1,1-dimethylpentyl)-4-hydroxy-2-methylbenzoic acid, 5-(1-methyl-1-ethylbutyl)-4-hydroxy-2-methylbenzoic acid, 5-(1,1-dimethylhexyl)-4-hydroxy-2-methylbenzoic acid, 5-(1-methyl-1-ethylpentyl)-4-hydroxy-2-methylbenzoic acid, 5-(1,1-dimethyl-3,3-dimethylbutyl)-4-hydroxy-2-methylbenzoic acid, 3,5-dibutyl-4-hydroxy-2-methylbenzoic acid, sodium salt of 5-t-butyl-4-hydroxy-2-methylbenzoic acid, sodium salt of 5-(1,1-dimethyl-3,3-dimethylbutyl)-4-hydroxy-2-methylbenzoic acid, sodium salt of 5-(1,1-dimethylbutyl)-4-hydroxy-2-methylbenzoic acid, sodium salt of 3,5-di-t-butyl-4-hydroxy-2-methylbenzoic acid, potassium salt of 5-t-butyl-4-hydroxy-2-methylbenzoic acid, potassium salt of 5-(1,1-dimethyl-3,3-dimethylbutyl)-4-hydroxy-2-methylbenzoic acid, potassium salt of 5-(1,1-dimethylbutyl)-4-hydroxy-2-methylbenzoic acid, and potassium salt of 3,5-di-t-butyl-4-hydroxy-2-methylbenzoic acid are preferred, and 5-t-butyl-4-hydroxy-2-methylbenzoic acid, sodium salt of 5-t-butyl-4-hydroxy-2-methylbenzoic acid, and potassium salt of 5-t-butyl-4-hydroxy-2-methylbenzoic acid are particularly preferred.

<Regarding Step (II)>

The reaction of the step (II) is a step of dealkylating the compound represented by general formula (2) obtained in the step (I).

(Catalyst)

The reaction of the step (II) can be carried out in the presence of a catalyst. Specific examples of catalysts that can be used include sulfuric acid; sulfonic acids such as para-toluenesulfonic acid, methanesulfonic acid, and trifluoromethanesulfonic acid; and Lewis acids such as aluminum chloride (III), boron trifluoride, and iron bromide (III). In particular, the reaction is preferably carried out in the presence of aluminum chloride (III) because the reaction proceeds efficiently in a short time.

The amount of catalyst used can be selected from the range of 0.01 to 5 times the amount of the compound represented by general formula (2) on a molar basis. When the catalyst used is a Lewis acid, the amount thereof is preferably 1 to 3 times, more preferably 2 to 3 times, on a molar basis. When the catalyst used is a sulfonic acid, the amount thereof is preferably about 0.1 to 1 time on a molar basis.

(Reaction Solvent)

The reaction of the step (II) can be carried out in a slurry state or a solution state. Specific examples of reaction solvents that can be used include aliphatic hydrocarbons typified by hexane, heptane, octane, nonane, decane, undecane, dodecane, ligroin, and kerosene; aromatic hydrocarbons typified by benzene, toluene, xylene, mesitylene, ethylbenzene, cumene, and naphthalene; and halogen-containing solvents such as dichloromethane, chloroform, and chlorobenzene.

The amount of reaction solvent used is not particularly limited, and in terms of economic efficiency, the amount is typically 0.1 or more times, preferably 0.5 to 100 times, more preferably 1 to 20 times the amount of the compound represented by general formula (2) on a weight basis.

(Reaction Conditions)

The reaction temperature in the step (II) can be freely selected according to the catalyst and reaction solvent used. For example, when a Lewis acid catalyst is used, the reaction temperature is 20° C. to 80° C., preferably 25° C. to 60° C., more preferably 30° C. to 50° C. When a sulfonic acid catalyst is used, the reaction temperature is 80° C. to 200° C., preferably 100° C. to 190° C., more preferably 120° C. to 180° C.

The reaction pressure in the step (II) may be normal pressure or reduced pressure. The reaction is preferably carried out under reduced pressure because generated hydrocarbon gas can be efficiently removed out of the reaction system. If the reaction is carried out under normal pressure, generated hydrocarbon gas can be efficiently removed out of the reaction system by carrying out the reaction while flowing a small amount of inert gas through the reaction system.

The reaction of the step (II) can be carried out for a time in the range of 1 to 24 hours according to the catalyst and reaction solvent used while observing the progress of the reaction as appropriate. If the reaction time is short, the reaction may fail to proceed sufficiently, and if the reaction time is long, an unintended reaction may proceed, leading to poor selectivity.

(Post-Reaction Treatment)

When a catalyst is used in the reaction of the step (II), a post treatment according to the catalyst used is necessary after completion of the reaction. The post treatment according to the type of catalyst can be performed in accordance with a known method.

For example, when aluminum chloride (III) is used as a catalyst, aluminum hydroxide formed as a result of reaction between water used in the post treatment and anhydrous aluminum chloride needs to be dissolved in water by using an acid to be separated from the object. Any acid can be used as long as it is an acid defined as a Bronsted acid, and specific examples include inorganic acids such as hydrochloric acid, sulfuric acid, nitric acid, and phosphoric acid; and organic acids such as oxalic acid, citric acid, and acetic acid. In particular, hydrochloric acid and sulfuric acid are preferred. These may be used in any combination. The amount of acid used is preferably an excess amount relative to aluminum chloride (III) used. If a sufficient amount of acid is not added, the object will not precipitate. In adding an acid, a solvent may be used in addition to the reaction solvent. The solvent used is preferably a solvent that poorly dissolves the object, and specific examples include aliphatic hydrocarbons typified by hexane, heptane, octane, nonane, decane, undecane, dodecane, ligroin, and kerosene; and aromatic hydrocarbons typified by benzene, toluene, xylene, mesitylene, ethylbenzene, cumene, and naphthalene. These may be used in any combination.

After the post treatment of the catalyst used, a known method can be used in order to isolate the object. For example, a precipitate of the object can be obtained in such a manner that the object is precipitated, for example, by adding a poor solvent to the solution that has been subjected to the post treatment of the catalyst and distilling off the solvent or, in the case where aluminum chloride (III) has been used as a catalyst as described above, by mixing the solution with a solution containing an acid, and the object is separated by filtration.

The precipitate obtained can be further purified by a method such as recrystallization. The purification by recrystallization is preferably performed using a good solvent and a poor solvent in combination. The good solvent may be, for example, an alcohol solvent such as methanol, ethanol, or propanol or a ketone solvent such as acetone or methyl isobutyl ketone, and the poor solvent may be, for example, water or a hydrocarbon solvent such as heptane, cyclohexane, or toluene.

<End Product: 4-Hydroxy-2-Methylbenzoic Acid>

According to the production method of the present invention, 4-hydroxy-2-methylbenzoic acid of interest can be obtained with a purity of 98.0% or more, preferably 98.5% or more, more preferably 99.0% or more.

EXAMPLES

The present invention will now be described more specifically with reference to Examples, but it should be noted that the present invention is not limited to these Examples.

The raw material conversion, reaction selectivity, and purity in Examples were analyzed by the following method.

1. Liquid Chromatography Apparatus, Analysis Conditions, and Method of Preparing Sample for Analysis
   Apparatus: Prominence UFLC manufactured by Shimadzu Corporation
   Pump: LC-20AD
   Column oven: CTO-20A
   Detector: SPD-20A
   Column: HALO C18
   Oven temperature: 50° ° C.
   Flow rate: 0.7 ml/min
   Mobile phase: (A) acetonitrile, (B) 0.1 wt % phosphoric acid aqueous solution
   Gradient conditions: (A) % by volume (time from start of analysis)
   20% (0 min)→40% (5 min)→100% (5 min)→100% (2 min)
   Sample injection volume: 3 μl
   Detection wavelength: 280 nm and 254 nm <Reaction Solution Analysis>

Accurately weigh a reaction solution into a 50 ml measuring flask. Add water (10 ml) and 85% phosphoric acid (one drop) in sequence and adjust to a marked line with acetonitrile. If $AlCl_3$ is contained, filter through a syringe filter.

<Crystal Analysis>

Accurately weigh a crystal into a 50 ml measuring flask, and adjust to a marked line with acetonitrile.

2. Method for Calculating Reaction Selectivity

"Reaction selectivity (%)"=(amount of object in reaction solution)÷(total amount of object and by-product in reaction solution)×100

"Amount of object in reaction solution" and "total amount of object and by-product in reaction solution" in the above formula were calculated using the absolute calibration method from values obtained by liquid chromatography.

<Regarding Absolute Calibration Method>

Calibration curves preliminarily calculated from concentrations (four concentrations: 1, 2, 10, and 30 mg/50 ml) in the above analysis method were constructed for raw materials, the object, and impurities. A reaction solution (crystal) was sampled, and a solution diluted with acetonitrile was prepared using a 50 ml measuring flask. Using the calibration curves, the concentration after dilution was calculated from an area value obtained by the analysis, and the weight of each composition contained in the reaction solution (crystal) was calculated, thereby deriving the raw material conversion and selectivity described below.

Reference Example 1 (Synthesis of Potassium Salt of 2-t-butyl-5-methylphenol)

A recovery flask was charged with 70.0 g (0.43 mol) of 2-t-butyl-5-methylphenol and 53.9 g (0.47 mol) of a 48.8% aqueous potassium hydroxide solution, and water in the system was sufficiently distilled off with a rotary evaporator at a temperature of 180° C. and a pressure of 1.2 kPa over 2 hours or more. The resulting solid was pulverized with a mortar in a dry nitrogen gas atmosphere to obtain 86.1 g of potassium salt of 2-t-butyl-5-methylphenol as a white powder.

The reaction selectivity in the step (I) due to the presence of the substituent "$R_1$" in general formula (1) of the present invention was investigated in Example 1 and Comparative Example 1.

Example 1

A four-necked flask was charged with 12.1 g (0.06 mol) of the potassium salt of 2-t-butyl-5-methylphenol obtained in Reference Example 1 and 88.2 g (0.54 mol) of 2-t-butyl-5-methylphenol. The temperature was raised to 70° C., and the reaction was carried out for 5 hours with stirring while blowing carbon dioxide onto the liquid surface. The composition of the resulting final reaction solution was analyzed by the absolute calibration method using liquid chromatography to show that the selectivity of 5-t-butyl-4-hydroxy-2-methylbenzoic acid in the reaction was 19%.

Comparative Example 1

An autoclave was charged with 13.3 g (0.09 mol) of potassium salt of m-cresol obtained in the same manner as in Reference Example 1 and 50.0 g of light oil, and the reaction was carried out at 170° C. to 200° C. for 5 hours while blowing carbon dioxide. The composition of the resulting final reaction solution was analyzed by the absolute calibration method using liquid chromatography to show that 4-methylsalicylic acid was obtained as a major product in 42.1% yield. The selectivity of 4-hydroxy-2-methylbenzoic acid in this reaction was 0%.

<Discussion on Reaction Selectivity>

It was found from the results of Example 1 above that in the Kolbe-Schmitt reaction using 2-t-butyl-5-methylphenol as a starting material, 5-t-butyl-4-hydroxy-2-methylbenzoic acid, in which a carboxyl group is selectively introduced at the para position of a phenolic hydroxyl group, is obtained at a temperature (70° C. in Example 1) much lower than the conventional Kolbe-Schmitt reaction temperature.

In contrast, it was found from the results of Comparative Example 1 that when the Kolbe-Schmitt reaction is carried out using m-cresol (3-methylphenol) as a starting material, 4-hydroxy-2-methylbenzoic acid, in which a carboxyl group is introduced at the para position of a phenolic hydroxyl group, cannot be obtained at all even at a high temperature of 170° C. to 200° C. as in the conventional reaction, and only 4-methylsalicylic acid, in which a carboxyl group is introduced at the ortho position of a phenolic hydroxyl group, is obtained.

It was revealed from the results of Example 1 and Comparative Example 1 that the presence of the alkyl group $R_1$ in the compound represented by general formula (1) in the present invention allows a carboxyl group to be selectively introduced at the para position of a phenolic hydroxyl group at a reaction temperature much lower than the conventional Kolbe-Schmitt reaction temperature.

Next, improvement in reaction efficiency in the step (I) was studied as described below.

Example 2

A recovery flask was charged with 50.0 g (0.30 mol) of 2-t-butyl-5-methylphenol and 38.9 g (0.34 mol) of a 48.8% aqueous potassium hydroxide solution, and water in the system was sufficiently distilled off with a rotary evaporator at a temperature of 180° C. and a pressure of 1.2 kPa over 2 hours or more. The resulting solid was pulverized with a mortar in a dry nitrogen gas atmosphere to obtain 59.4 g of potassium salt of 2-t-butyl-5-methylphenol as a white powder.

Next, a four-necked flask was charged with 12.0 g (0.06 mol) of the synthesized potassium salt of 2-t-butyl-5-methylphenol and 100.1 g of dimethylformamide dehydrated with a molecular sieve 4A (manufactured by NACALAI TESQUE, INC.). The temperature was raised to 70° C., and the reaction was carried out for 16 hours with stirring while blowing carbon dioxide onto the liquid surface. The composition of the resulting final reaction solution was analyzed by the absolute calibration method using liquid chromatography to show that the selectivity of 5-t-butyl-4-hydroxy-2-methylbenzoic acid in the reaction was 94%.

Example 3

A four-necked flask was charged with 102.5 g (0.62 mol) of 2-t-butyl-5-methylphenol, 78.9 g (0.69 mol) of a 48.8% aqueous potassium hydroxide solution, 204.8 g of 1,3-dimethyl-2-imidazolidinone, and 153.7 g of toluene and equipped with a Dean-Stark apparatus. The reaction was then carried out with stirring at a temperature of 90° C. or higher over 5 hours to sufficiently distill off water in the system. The Dean-Stark apparatus was then replaced with a distillation pipe, and toluene in the system was recovered at a temperature of 135° C. (87% toluene recovery).

After completion of the recovery, the system was cooled to 70° C., and the reaction was carried out for 26 hours with stirring while blowing carbon dioxide onto the liquid surface. To the resulting final reaction solution, 361.3 g of water, 75.9 g of 35% hydrochloric acid water, and 128.1 g of cyclohexane were added with stirring to precipitate a solid. The precipitated solid was filtered, and the residue was washed with 160.0 g of cyclohexane and 160.0 g of water and dried to obtain 64.1 g of a white crystal with a purity of 95.8%. The yield relative to converted 2-t-butyl-5-methylphenol was 73%, and the composition of the resulting final reaction solution was analyzed by the absolute calibration method using liquid chromatography to show that the selectivity of 5-t-butyl-4-hydroxy-2-methylbenzoic acid in the reaction was 86%.

As a result of NMR and LC-MS, the white solid obtained was determined to be a reaction intermediate of interest having the following chemical structure.

[Chem. 4]

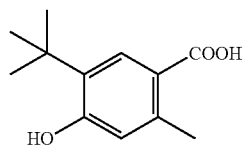

Melting point: 149.6° C. (by differential scanning calorimetry)
Molecular weight: 208.26
Identification by proton NMR (400 MHz, solvent: DMSO-d6, internal standard: tetramethylsilane)
Chemical shift (signal shape, proton number): 1.33 ppm (s, 9H), 2.41 ppm (s, 3H), 6.65 ppm (s, 1H), 7.76 ppm (s, 1H), 9.99 (s, 1H, —OH), 12.20 (s, 1H, —COOH).

Example 4

A four-necked flask was charged with 20.0 g (0.12 mol) of 2-t-butyl-5-methylphenol, 15.4 g (0.13 mol) of a 48.8% aqueous potassium hydroxide solution, 60.0 g of N-methyl-2-pyrrolidone, and 45.1 g of toluene and equipped with a Dean-Stark apparatus. The reaction was then carried out with stirring at a temperature of 100° C. or higher over 3.5 hours to sufficiently distill off water in the system. The Dean-Stark apparatus was then replaced with a distillation pipe, and toluene in the system was recovered at a temperature of 135° C. (87% toluene recovery).

After completion of the recovery, the system was cooled to 70° C., and the reaction was carried out for 13 hours with stirring while blowing carbon dioxide onto the liquid surface. The composition of the resulting final reaction solution was analyzed by the absolute calibration method using liquid chromatography to show that the selectivity of 5-t-butyl-4-hydroxy-2-methylbenzoic acid in the reaction was 91%.

Example 5

A four-necked flask was charged with 24.1 g (0.12 mol) of the potassium salt of 2-t-butyl-5-methylphenol obtained in Reference Example 1, 19.6 g (0.12 mol) of 2-t-butyl-5-methylphenol, and 48.4 g of dimethylformamide dehydrated with a molecular sieve 4A (manufactured by NACALAI TESQUE, INC.). The temperature was raised to 70° C., and the reaction was carried out for 5 hours with stirring while blowing carbon dioxide onto the liquid surface. The composition of the resulting final reaction solution was analyzed by the absolute calibration method using liquid chromatography to show that the selectivity of 5-t-butyl-4-hydroxy-2-methylbenzoic acid in the reaction was 91%.

Example 6

A four-necked flask was charged with 20.3 g (0.10 mol) of the potassium salt of 2-t-butyl-5-methylphenol obtained in Reference Example 1 and 40.5 g of dimethylsulfoxide dehydrated with a molecular sieve 4A (manufactured by NACALAI TESQUE, INC.). The temperature was raised to 70° C., and the reaction was carried out for 23 hours with stirring while blowing carbon dioxide onto the liquid surface. The composition of the resulting final reaction solution was analyzed by the absolute calibration method using liquid chromatography to show that the selectivity of 5-t-butyl-4-hydroxy-2-methylbenzoic acid in the reaction was 99%.

Comparative Example 2

Potassium salt of m-cresol in an amount of 12.0 g (0.08 mol) obtained in the same manner as in Reference Example 1 and dimethylformamide in an amount of 100.0 g dehydrated with a molecular sieve 4A (manufactured by NACALAI TESQUE, INC.) were charged, and the reaction was carried out at 90° C. for 7 hours while blowing carbon dioxide. The composition of the resulting final reaction solution was analyzed by the absolute calibration method using liquid chromatography to show that the selectivity of 4-hydroxy-2-methylbenzoic acid was 38%. The selectivity of 4-methylsalicylic acid was 62%, and the raw material conversion was 32%.

<Discussion on Study on Improvement in Reaction Efficiency>

It was found from the results of Examples 2 to 6 above that when the Kolbe-Schmitt reaction is carried out in an aprotic polar solvent using 2-t-butyl-5-methylphenol as a starting material, 5-t-butyl-4-hydroxy-2-methylbenzoic acid, in which a carboxyl group is selectively introduced at the para position of a phenolic hydroxyl group, is obtained with a selectivity as high as 80% or more at a temperature much lower than the conventional Kolbe-Schmitt reaction temperature.

In contrast, it was found from the results of Comparative Example 2 that when the Kolbe-Schmitt reaction is carried out in an aprotic polar solvent using m-cresol (3-methylphenol) as a starting material, 4-hydroxy-2-methylbenzoic acid, in which a carboxyl group is introduced at the para position of a phenolic hydroxyl group, is formed, but with a selectivity as low as 38%. The selectivity of 4-methylsalicylic acid, in which a carboxyl group is introduced at the ortho position of a phenolic hydroxyl group, is 62%, which is much higher than the selectivity at the para position, and, moreover, the raw material conversion is as low as 32%, thus revealing that this method is not practical at all as a production method for obtaining 4-hydroxy-2-methylbenzoic acid of interest.

The step (II) of the present invention was performed.

Example 7: Step (II)

Synthesis of 4-hydroxy-2-methylbenzoic Acid

In 638.8 g of toluene was dissolved 64.1 g (0.31 mol) of the intermediate 5-t-butyl-4-hydroxy-2-methylbenzoic acid obtained in Example 3 above, and 122.8 g (0.92 mol) of anhydrous aluminum chloride (III) was added and allowed to react at 40° C. for 16 hours. Water in an amount of 462.3 g was added thereto in an ice bath to form an orange gel-like reaction solution. Then, 63.8 g of 35% hydrochloric acid water was added to precipitate a crude object as a light brown solid. The precipitated crude object was recovered by filtration and purified with methanol and water to thereby obtain 4-hydroxy-2-methylbenzoic acid with a purity of 99.5% as a white crystal. The yield relative to 5-t-butyl-4-hydroxy-2-methylbenzoic acid was 82%.

As specifically described in Examples 1 to 7 above, the production method according to the present invention, as compared to the Kolbe-Schmitt reaction known in the art, can selectively provide 4-hydroxy-2-methylbenzoic acid with efficiency under very mild reaction conditions and thus has been shown to be a very advantageous method as an industrial production method.

In addition, since the use of an aprotic polar solvent as a reaction solvent in the step (I) of the present invention further improves reaction efficiency, the method has also been confirmed to be very useful as an industrial production method.

The invention claimed is:

1. A production method for 4-hydroxy-2-methylbenzoic acid, comprising performing a step (I) of reacting a compound represented by general formula (1) below with carbon dioxide to introduce a carboxyl group selectively at a para position of the $OR_2$ group, relative to a ortho or a meta position of the $OR_2$ group, in a reaction solution so as to obtain a compound represented by general formula (2) below, and then a step (II) of dealkylating the compound represented by general formula (2):

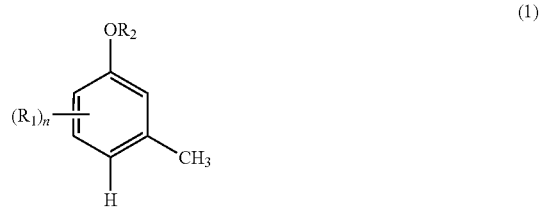

wherein $R_1$ represents a branched alkyl group having 3 to 8 carbon atoms or a cyclic alkyl group having 5 to 6 carbon atoms, $R_2$ represents a hydrogen atom or an alkali metal, n is 1, and $R_1$ is at an ortho position of the $OR_2$ group, which is a para position of the $CH_3$ group, and

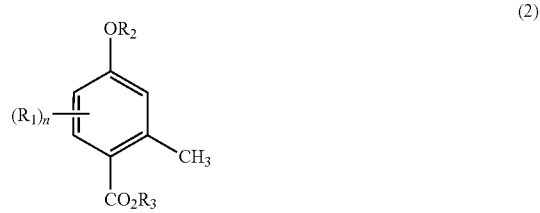

wherein $R_1$, $R_2$, and n are as defined in general formula (1), and $R_3$ represents a hydrogen atom or an alkali metal, and $R_1$ is at the ortho position of the $OR_2$ group, which is the para position of the $CH_3$ group.

2. The production method according to claim 1, wherein an aprotic polar solvent is used as a reaction solvent in the step (I).

* * * * *